United States Patent [19]

Mathur

[11] Patent Number: 4,941,459

[45] Date of Patent: Jul. 17, 1990

[54] DENTAL HYGIENE DEVICE

[76] Inventor: Sandip K. Mathur, 13 Sherka Crescent, Kanata, Ontario, Canada, K2K 2L4

[21] Appl. No.: 375,908

[22] Filed: Jun. 7, 1989

[51] Int. Cl.⁵ ............................................. A61G 17/02
[52] U.S. Cl. ......................................... 128/66; 433/88
[58] Field of Search ................. 128/66, 62 A; 433/80, 433/88

[56] References Cited

U.S. PATENT DOCUMENTS

| | | | |
|---|---|---|---|
| 1,646,942 | 10/1927 | Tuorto | 128/66 |
| 2,757,668 | 8/1956 | Meyer-Saladin | 128/62 A |
| 2,957,476 | 10/1960 | Freeman | 128/66 |
| 3,110,445 | 11/1963 | Benjamin et al. | 239/428.5 |
| 3,468,306 | 9/1969 | Heitzman | 128/66 |
| 3,481,676 | 12/1969 | Schwartzman | 401/134 |
| 3,669,101 | 6/1972 | Kleiner | 604/150 |
| 3,687,561 | 10/1972 | Phillips | 401/134 |
| 3,828,771 | 8/1974 | Gartner | 128/62 A |
| 3,910,706 | 10/1975 | Del Bon | 401/134 |
| 4,415,288 | 11/1983 | Gordon et al. | 401/132 |
| 4,564,005 | 1/1986 | Marchand et al. | 128/66 |
| 4,753,260 | 6/1988 | Gibbs | 137/14 |

Primary Examiner—John J. Wilson

[57] ABSTRACT

A oral hygiene device that is used for cleaning teeth to prevent cavities, for removing plaque, and for massaging the gums. The device is attachable directly to a pressurized water supply such as a faucet. A high velocity jet of water is provided so that it is possible to clean out food particles in the teeth and to stimulate blood circulation in the gums. The device includes a coupling for connection to a faucet, aerator, a cartridge holding component, and a handle; cartridges containing concentrated solutions such as mouthwash, fluoride, baking soda, salt, or specialized solutions recommended by dentists are insertable into the holding component which can be a separate component located at the faucet or it can form part of the handle. The aerator can be in the handle component to create bubbles in order to create a pulsating effect. A movable button in the handle is used to control the rate of flow of the fluid.

12 Claims, 4 Drawing Sheets

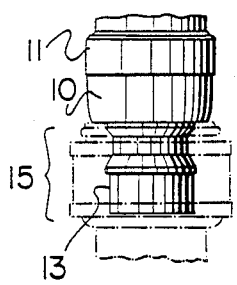
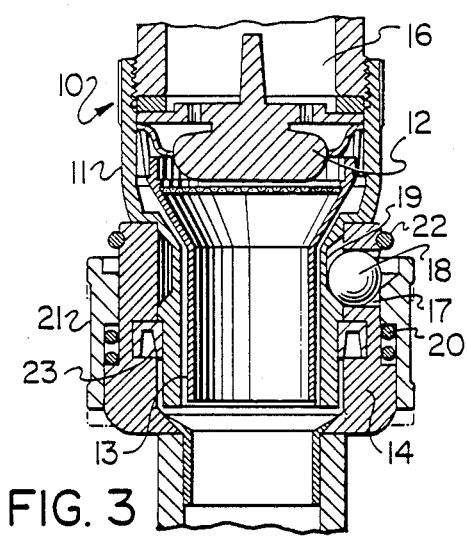
FIG. 2
FIG. 3
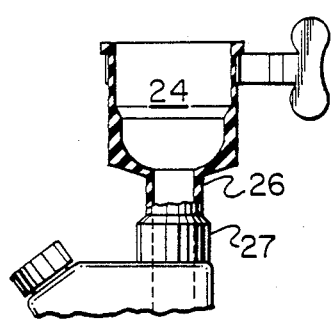
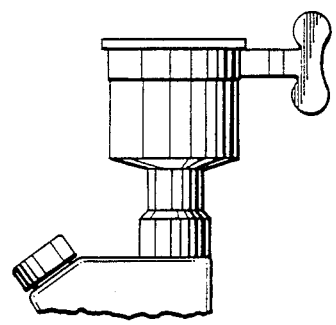
FIG. 4
FIG. 4B

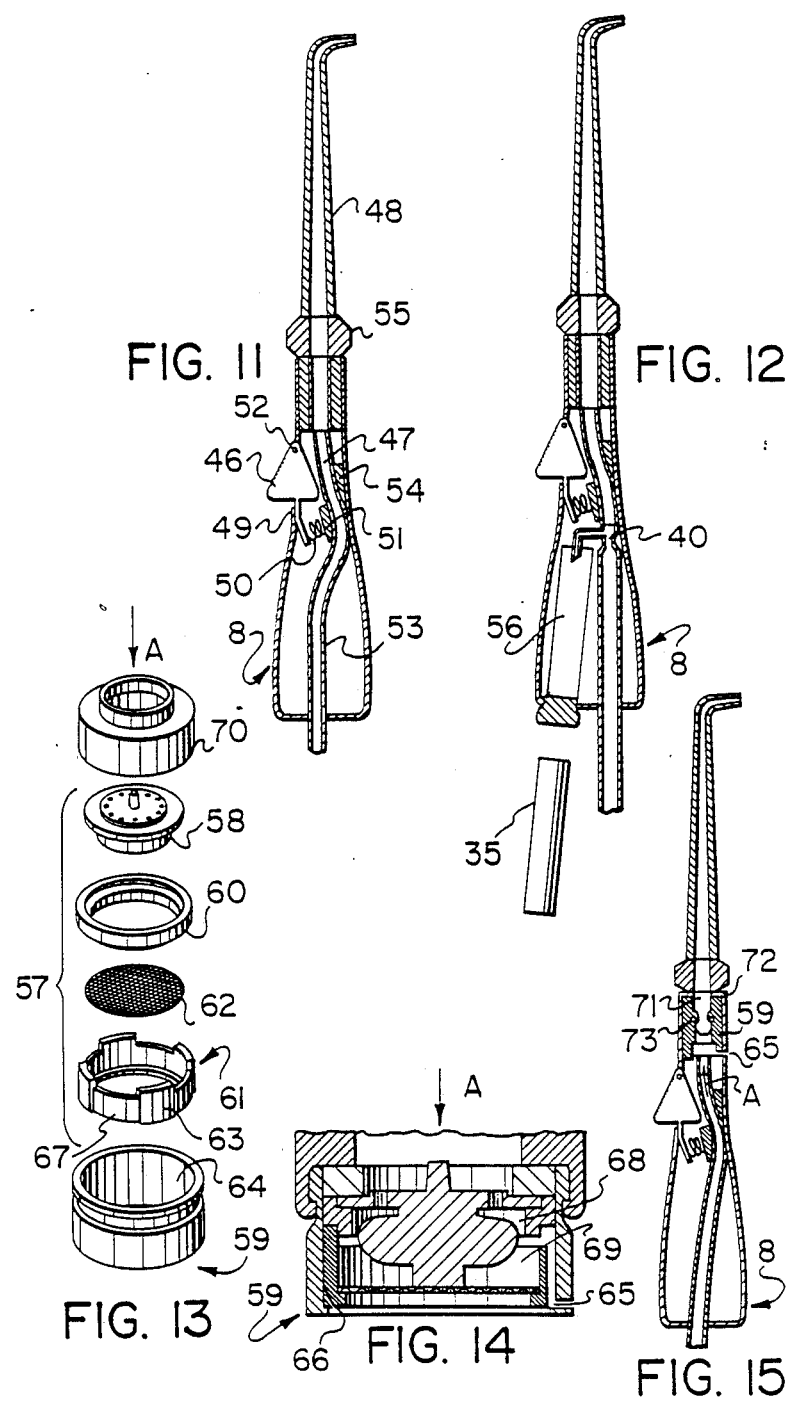

DENTAL HYGIENE DEVICE

FIELD OF INVENTION

The present invention relates to improvements in oral irrigation for dental hygiene.

BACKGROUND OF THE INVENTION

Dentists have long been using water jets for the purpose of flushing mouths during teeth cleaning. The use of water jets in the home for personal oral hygiene has been found to be of significant benefit in cleaning teeth and dislodging foreign matter and plaque in areas around the teeth. These areas around the teeth and gums are not easily accessed by brushing and flossing.

The several types of devices that have been proposed for the purpose of oral irrigation can be broadly categorized into those which are electrically-operated pump devices and those which are directly attachable to a pressurized water source such as a faucet. The electrically-operated device involves the use of a pulsating jet of water fed to a hand held syringe by a pump which is placed beside a bathroom sink. These devices may be unsafe if the pump component is submerged completely in water (in the event of an accident) since this may pose a shock hazard. Also these devices take up considerable space in a limited-spaced bathroom environment. The bulky nature of these units poses a problem in carrying these units while travelling. Still another drawback of these devices is that an on-off switch is located on the pump (and not on the hand held component) and therefore is incovenient to access while the jet tip is in the mouth.

Known devices which are attachable directly to a water source also have several disadvantages. Some of these devices do not have pulsating capabilities and those which do employ complex mechanisms. Most of the known devices lack the ability to control the rate of water aside from usual tap rotation. Some of the known devices lack the ability to connect to a majority of the different faucets and those which do are largely inconvenient or involve complex procedures. Lastly, most of these devices lack appropriate clamping and securing measures of devices to faucets to avoid slippage while in use.

SUMMARY OF THE INVENTION

An object of the present invention is to provide cartridges containing dental care solutions which can be inserted into the device. The solution inside the cartridge will be slowly drawn out and mixed with the water flowing from the faucet.

Another object is to provide a convenient method and apparatus for the connection of the device to a faucet opening. The male threaded aerator member will become a permanent attachment of the faucet assembly and the female coupling will snap onto and out of the threaded male aerator member.

Another object of the present invention is to provide a pulsation effect using an aerator assembly to create bubbles or a paddle wheel assembly to create spurts of fluid.

Another object of the invention is to provide a pulsation effect using an aerator assembly to create bubbles or a paddle wheel assembly to create spurts of fluid.

Another object of the invention is to provide a device which is convenient to use and store. The wall-mounting bracket will provide a facility to place and store the device while not in use.

Still another object of the invention is to provide an effective oral hygiene product which is economical, safe, easy to use and easy to manufacture.

In keeping with the foregoing there is provided in accordance with the present invention an oral hygiene device that includes a handle having a nozzle applicator detachably mounted at one end thereof and a flexible hose connected to said nozzle applicator. The flexible hose has a nozzle coupling means on the opposite end thereof for detachable connection to a faucet outlet nozzle. Means is provided for introducing air into a stream of water flowing from the faucet through the device to the nozzle applicator. The aerator means may be located either at the faucet nozzle coupling or in the handle. The aerator, means when located in the handle, is removably inserted into a cavity in the handle in press fit relation upstream of the detachable applicator nozzle. A cartridge receiving chamber is provided and which communicates with a stream of water flowing through the device. The cartridge receiving chamber can be located either in the handle or in a separate device located in proximity to the faucet nozzle coupling. The cartridge receiving chamber has means therein for puncturing the cartridge for releasing the contents therefrom and means is provided for introducing a mouth treatment fluid released from the cartridge into the stream of water flowing through the device which includes a venturi through which the main stream of water flows.

LIST OF DRAWINGS

The invention is illustrated by way of example in the accompanying drawings wherein:

FIG. 2 is an elevational view of the coupling portion that attaches to a faucet discharge;

FIG. 3 is a sectional view of the male and female portions of the coupling;

FIG. 4 is a sectional view, illustrating another coupling member;

FIG. 4B is a full view of the coupling member of FIG. 4;

FIG. 11 is a sectional view of the handle component;

FIG. 12 is a sectional view of an alternate handle component housing a cartridge opening;

FIG. 13 is an exploded view of the aerator assembly housed in the handle component;

FIG. 14 is a sectional view of the aerator assembly housed in the handle component; and FIG. 15 is a sectional view depicting the aerator assembly in the handle component and depicting a snap-on attachment method of the nozzle to the handle.

DETAILED DESCRIPTION OF PREFERRED EMBODIMENT

Figure 1:
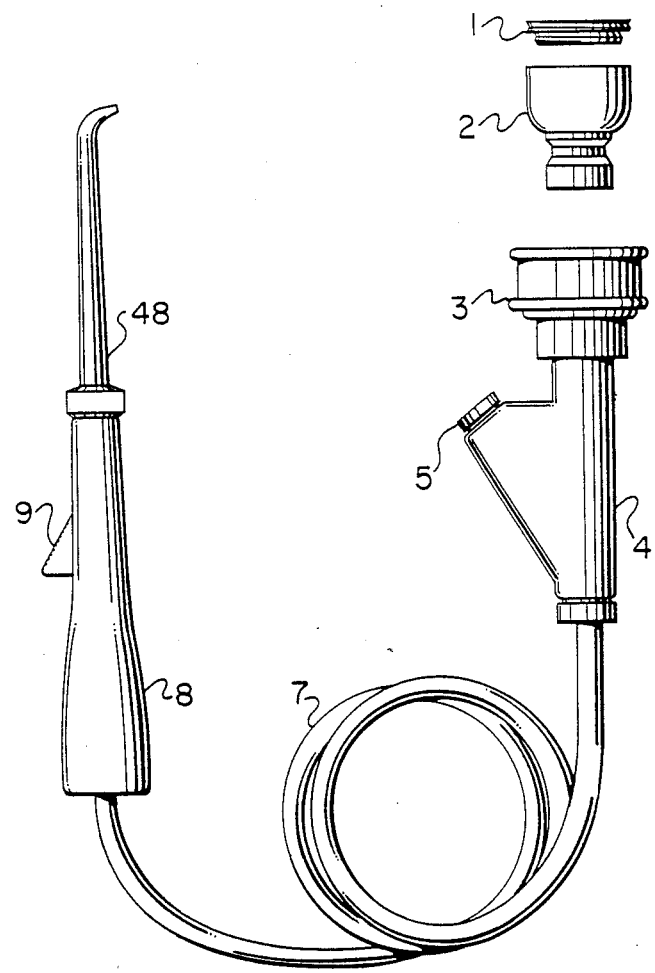
FIG. 1 is a partially exploded view of the overall device.

The hygiene device of the present invention illustrated in FIG. 1, includes a handle portion 8 connected by a flexible hose 7 to a cartridge holding device 4. The handle 8 has a nozzle 48 detachably connected thereto and the cartridge holding component 4 is attachable to the discharge end of a faucet nozzle by a male/female coupling. In FIG. 1 the male coupling 2 is shown detached from the female coupling portion 3. The male coupling 2 is detachably connected to the discharge end of the faucet nozzle by way of an adapter or screw fit coupling 1.

Figure 5:
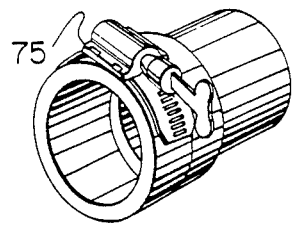
FIG. 5 is an oblique view of a coupling with a screw-type clamp.

The cartridge holding component 4 provides means whereby concentrated solutions such as a mouthwash, fluoride, baking soda, salt or specialized solutions recommended by the dentist may be incorporated into the flowing water before discharge as a high velocity jet from the nozzle 48. As will be seen hereinafter, the cartridge holding component can be incorporated into the handle portion 8 in which case the hose 7 is directly coupled to the faucet nozzle by suitable means such as the quick disconnect coupling illustrated in FIG. 1 or a clamp-on coupling as illustrated in FIGS. 4 and 5.

The coupling to the faucet is an aerator type, quick disconnected, details of which are illustrated in FIGS. 2 and 3. Referring to these drawings there is a threaded faucet attachment device 10 that has a tubular casing 11 with an aerator enclosing 12 and a lower coupling portion 13. The lower coupling portion 13 is adapted to receive and retain a female portion 14 a snap-on coupling fitting 15. The upper end of the casing portion 11 is threaded to allow engagement of the device to a faucet 16. Universal adapters 1 having several dimensions of internal and external threads will be provided for connection of the faucet attachment device 10 to various faucet openings.

The upper end of the portion 14 is provided with three circumferentially spaced radially protruding cavities or bores 17. A ball 18 which has a dimension greater than the wall thickness of the portion 14 is mounted in each bore 17. The balls 18 have the capacity to be shifted radially inward in their respective bores 17 in order to mount the female coupling portion 14 on the annular grooves 19 of the male coupling portion 13.

A coil spring 20 is provided between portions of the sleeve 21 and the coupling portion 14 to urge the sleeve 21 upward. A snap ring 22 is placed around the upper end of the coupling portion 14 to prevent disengagement of the sleeve 21 when the fitting 14 is removed from the device 10. A rubber seal 23 prevents fluid leakage between the coupling portions 13 and 14 when the fitting 15 is engaged with the device 10.

Figure 6:
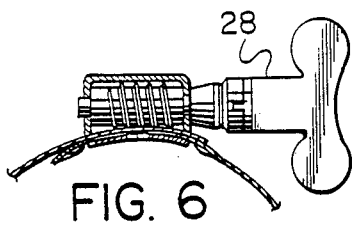
FIG. 6 is a detailed sectional view of the clamp of FIG. 5.

An alternate faucet attachment method as seen in FIG. 4 is composed of a rubber sleeve member 24 which fits over a faucet aerator member 25. The sleeve member 24 is shaped to form an opening 26 with a smaller diameter at the down-stream end than at the upstream end. A male coupling portion 27 which is attached to the sleeve member 24 is also attached to the cartridge holding component 4. As seen in FIGS. 5 and 6 a screw-type clamp 75 with a key attachment 28 that rotates is provided to secure the rubber sleeve member 24 around the faucet aerator member 25 while the device is in use.

Figure 7:
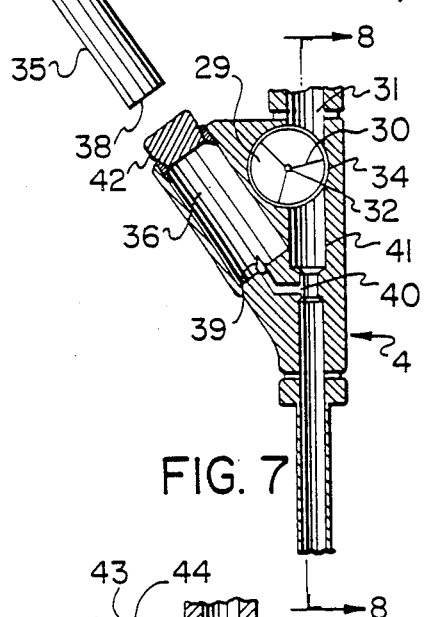
FIG. 7 is a sectional view of a cartridge holding component of the device.
Figure 8:
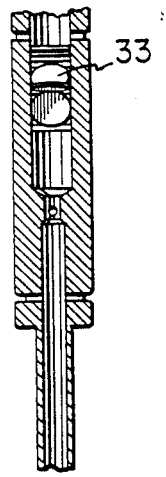
FIG. 8 is a stepped sectional view taken essentially along line 8—8 of FIG. 7.

Referring to FIGS. 7 and 8 the cartridge holding component 4 has a circular cavity or space 29 in which a paddle wheel 30 can spin when driven by fluid passing downward through the component opening 31. The paddle wheel 30 is mounted on an axle 32 which allows rotation of the paddle wheel 20. Each blade 33 of the paddle wheel 30 is forced by the downward passing fluid to be pushed down breaking the flow of fluid. Each blade slaps a disrupter 34 before releasing the entrapped fluid. The downward flow of the entrapped fluid is released in a spurt-like manner, creating a pulsating effect.

A cylindrical cartridge 35 containing dental hygiene fluid is provided to be inserted into the cartridge opening 36 which has a diameter somewhat larger than the cartridge diameter. A thin, small, circular are 38 located in the centre of the floor of the cartridge 35 is completely inserted into the cartridge opening 36. A small, cylindrical, angularly cut piercing tube 39 is protruding into the centre of the floor of the cartridge opening 36. The tip of the piercing tube 39 has a sharp narrow opening to facilitate penetration of the circular area 38 of the cartridge 35. The other end of the piercing tube is attached to a venturi section 40 in the passage tube 41. The low pressure area created by the venturi section draws the fluid contained in the cartridge 35 into the passage tube 41 to allow mixture with the passing fluid. A screw-top cap 42 is provided to securely contain the cartridge 35 in the cartridge opening 36 and to ensure complete penetration of the thin area 38 by the piercing tube 39.

Figure 9:
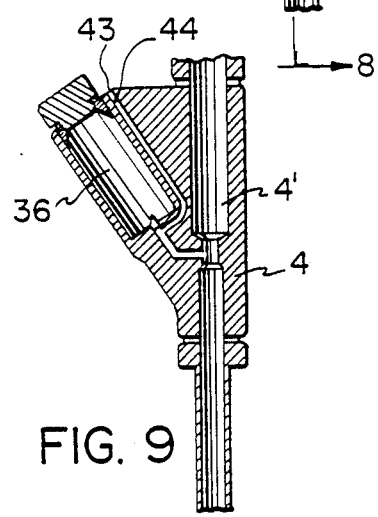
FIG. 9 is a sectional view of an alternate cartridge holding component depicting an air inlet passage.
Figure 10:
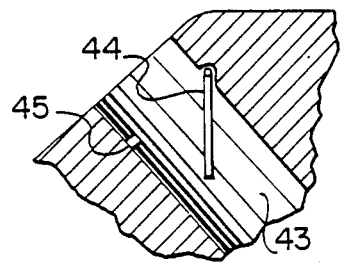
FIG. 10 is a detailed view of the flap mechanism seen in FIG. 9.

An alternate cartridge holding component 4 as seen in FIG. 9 contains an air inlet passage 43 at the top end of the cartridge opening 36. This air inlet allows air from the atmosphere to pass into the piercing tube 39 and mix the fluid which is passing through the primary passage 4'. This mixture of air will create bubbles in the passing fluid thereby creating a discontinuous flow of fluid. The result of this discontinuous flow is a pulsation effect. The air inlet passage will eliminate the need for a paddle wheel 30. Referring to FIG. 10, the top of the air inlet passage 43 can be provided with a valve in the form of a flap 44 in order to prevent any fluid from escaping out of the air inlet passage 43. A block 45 provides a stop for the flap 44 which can be resiliently biased thereagainst either by the springiness of the flap or by a separate spring.

Referring to FIG. 11 the handle component 8 contains a button 46 which can be pressed inward in order to push the walls of the flimsy hose 47 to meet. This temporary collpase of the flimsy hose 47 will cause a blockage in the flow of fluid passing from the main tube 7 to the nozzle 48. An extension arm 49 which is attached to the button 46 enables a spring 50 to push the button into an upward position. A spring support block 51 provides a base for the spring 50. The button 46 is attached to the handle component 8 by an axle 52 that allows rotation of the button 46 from an upward or open position to a downward pressed or close position defined by the travel limitation of the extension arm 49. The flimsy hose 47 is connected to a strong hose 53 at either end. A hose support block 54 provides a base for which the walls of the flimsy hose 47 can be pressed together when the button 46 is pressed downward or in a close position. The flimsy hose 47 expands to its full natural diametrical size when the button 46 is released and in its open position, allowing full flow of fluid into the nozzle 48. A nozzle 48 provided at the end of the handle component 8 is curved at an angle of about 80 degrees near the tip. The tip of the nozzle 48 consists of a small opening which creates a high velocity of fluid passing through. The nozzle 48 is attached to a base 55 to secure it in place.

An alternate handle as seen in FIG. 12 contains a cartridge chamber 56 in the handle component 8. The methods of cartridge insertion, penetration of the cartridge, fluid mixture, and turning of the screw-top cap are identical to the method described hereinbefore.

Another alternative handle component 8 as seen in FIG. 15 provides an aerator which breaks up the flow of fluid which is passing through and introduces air into the fluid. The mixing of air and fluid results in a discontinuous flow of fluid creating a pulsation effect.

The assembly 57 includes an aerator plug or fluid break and mixing body 58 which breaks up the flow of fluid passing through the casing 74 and increases the flow velocity of the fluid. The aerator plug 58 is supported by an annular component or ring 60 which in turn is supported by a cylindrical cage 61. A metallic screen 62 is mounted in the downstream end position in the cylindrical cage 61. The cylindrical cage 61 includes several radially outward projecting ribs 63 which provide a close-fitting engagement with a smooth cylindrical with the inner surface 64 of the casing 59. The ribs 63 co-operate with the inner surface 64 to form accurately extending air inlet passages 65 which are circumferentially spaced and disposed between adjacent ribs 63. Each passage 65 is confined by the interior surface 66 and the concentric exterior surface of a web or circumferential wall component 67 of the cylindrical cage 61. The passages 65 extend axially upstream from the outlet to enable air to flow into the cylindrical cage from the surrounding atmosphere.

The aerator plug 58 along with the ring 60 provides a mixing zone 68 in which the air and fluid are mixed. As the jets of fluid pass through the mixing zone 68 air is drawn through the passages 65 and inwardly through the apertures 69 into the mixing zone 68 and mixed with the jets of fluid. The outer casing 70 snap-fits-over the lower casing 59 to house the assembly 57. The fitted casings 59 and 70 will be snap-fitted in an area of the handle component 8 as shown in FIG. 15. This alternate handle housing and aerator assembly eliminates the need for an air inlet passage or a paddle wheel 30 in the cartridge holder component 4 as seen in FIGS. 7 and 8. Arrow "A" designates the direction of fluid flow through the aerator and the device in FIGS. 13, 14 and 15. An alternative nozzle and base attachment method can be seen in FIG. 15. The attachment 71 snaps into the handle opening 72. A rubber O ring 73 is placed in the handle 8 to prevent leakage at the joint of the attachment 71 and the handle 8.

In the foregoing there is described and there is illustrated in the drawings a device for personal dental hygiene home use which is attachable to a water faucet. Air can be entrained in the flowing stream of water, either where the device attaches to the tap or alternatively by an aerator located in the handle portion of the device. Various means are illustrated for detachable connection to the faucet nozzle and a cartridge type dispenser is provided in a separate unit at the attachment to the faucet nozzle or alternatively in the handle portion of the device. A flow interrupter in the form of a paddle wheel is used to give a pulsating effect to the flowing stream.

A combination aerator and hose coupling device for attachment to the faucet is known from the teachings of U.S. Pat. No. 3,110,445 issued Nov. 12, 1963 to F. E. Benjamin, et al. A mechanical device for the pulsating device operative by the flow of water and suitable for use in the present device is disclosed in U.S. Pat. No. 3,468,306 issued Sept. 23, 1969 to C. J. Heitzman. Other alternative arrangements will be obvious to those skilled in the art, particularly taking into account the teachings of the following references:

| U.S. PAT. NOS. | ISSUE DATE |
| --- | --- |
| 3,425,410 | February 4, 1969 |
| 3,690,318 | September 12, 1972 |
| 3,828,771 | August 13, 1974 |
| 4,564,005 | January 14, 1986 |
| 4,452,238 | June 5, 1984 |
| 4,302,186 | November 24, 1981 |
| 4,135,501 | January 23, 1979 |
| 4,442,831 | April 17, 1984 |
| 4,793,331 | September 27, 1988 |
| 4,135,501 | January 23, 1979 |
| 4,265,229 | May 5, 1981 |
| 3,227,158 | January 4, 1966 |
| 3,973,558 | August 10, 1976 |
| 3,393,673 | July 23, 1968 |

I claim:
1. A hygiene device comprising:
 (a) a handle having a nozzle applicator at one end thereof;
 (b) a flexible hose connected at one end thereof to said nozzle applicator and having a faucet nozzle coupling means at the other opposite end thereof;
 (c) means for introducing air into a stream of water flowing through said device;
 (d) a chamber communicating with said stream of water flowing through said device, said chamber having a removal cap through which a cartridge containing a mouth treatment fluid can be introduced and including cartridge puncturing means in said chamber; and
 (e) means for introducing a mouth treatment fluid into said stream of water from said chamber.
2. An oral hygiene device as defined in claim 1 wherein said nozzle applicator is detachably mounted on said handle.
3. An oral hygiene device as defined in claim 1 wherein said aerator means is mounted in said handle.
4. An oral hgiene device as defined in claim 1 wherein said aerator means is located in said faucet nozzle coupling means.
5. An oral hygiene device as defined in claim 1 wherein said cartridge puncturing means comprises a tube having a sharpened edge projecting into said chamber from the passage means that provides communication between the chamber and the flowing stream of water.
6. An oral hygiene device as defined in claim 1 wherein said chamber is located in said handle.
7. An oral hygiene device as defined in claim 1 wherein said chamber is contained in a separate unit and wherein said separate unit is disposed in proximity of the faucet nozzle coupling means.
8. A hygiene device comprising:
 (a) a handle having a nozzle applicator at one end thereof;
 (b) a flexible hose connected at one end thereof to said nozzle applicator and having a faucet nozzle coupling means at the other opposite end thereof;
 (c) means for introducing air into a stream of water flowing through said device;

(d) a chamber communicating with said stream of water flowing through said device, said chamber being located in said handle and having a removable cover for introducing a cartridge containing a mouth treatment liquid into said chamber, cartridge puncturing means in said chamber; and (e) means for introducing a mouth treatment fluid into said stream of water from said chamber, said means comprising a venturi through which the flowing stream passes and wherein the passage means from the chamber terminates in said venturi.

9. An oral hygiene device as defined in claim 8 including a flexible hose portion in said handle through which the stream of water flows and a finger operative means for squeezing the flexible hose to flatten the same and thereby control the rate of fluid flow through the device.

10. A hygiene device as defined in claim 8 including means interrupting the flow of water at spaced intervals providing a pulsating discharge of water from the nozzle application during use of the device.

11. A hygiene device comprising:

(a) a handle having a nozzle applicator detachably mounted on one end thereof;

(b) a flexible hose communicating at one end thereof via passage means through said handle with said nozzle applicator and having a faucet nozzle coupling means at the outer opposite end thereof;

(c) means for introducing air into a stream of water flowing through said device to aerate such stream;

(d) a chamber in said handle communicating with said stream of water flowing through said device, said chamber having removable closure means for removably inserting a cartridge into said chamber and cartridge puncturing means in said chamber;

(e) venturi means in said passage through the handle for introducing a mouth treatment fluid contained in a cartridge in said chamber into said stream of water flowing to said nozzle applicator; and (f) means for causing pulsations in the flow of the flowing stream to said nozzle.

12. An oral hygiene device as defined in claim 11 including finger operative means on said handle for selectively controlling the rate of fluid flow through the device.

* * * * *